(12) United States Patent
Belhabib

(10) Patent No.: US 11,691,762 B2
(45) Date of Patent: Jul. 4, 2023

(54) METHOD AND A SYSTEM FOR MONITORING A LUBRICATED MECHANICAL SYSTEM

(71) Applicant: AIRBUS HELICOPTERS, Marignane (FR)

(72) Inventor: Gilles Belhabib, Aix en Provence (FR)

(73) Assignee: AIRBUS HELICOPTERS, Marignane (FR)

( * ) Notice: Subject to any disclaimer, the term of this patent is extended or adjusted under 35 U.S.C. 154(b) by 194 days.

(21) Appl. No.: 17/016,831

(22) Filed: Sep. 10, 2020

(65) Prior Publication Data
US 2021/0070474 A1    Mar. 11, 2021

(30) Foreign Application Priority Data

Sep. 10, 2019 (FR) ...................................... 1909954

(51) Int. Cl.
*B64F 5/60*      (2017.01)
*B64D 45/00*    (2006.01)
(Continued)

(52) U.S. Cl.
CPC ................ *B64F 5/60* (2017.01); *B64D 45/00* (2013.01); *F16H 57/0404* (2013.01);
(Continued)

(58) Field of Classification Search
CPC ... B64F 5/60; B64D 45/00; B64D 2045/0085; G01N 15/0606; G01N 15/0656;
(Continued)

(56) References Cited

U.S. PATENT DOCUMENTS

| | | | |
|---|---|---|---|
| 6,582,661 B1* | 6/2003 | Pardue | G01N 33/2888 422/50 |
| 2002/0148788 A1* | 10/2002 | Berns | F01M 1/10 210/167.02 |

(Continued)

FOREIGN PATENT DOCUMENTS

| | | |
|---|---|---|
| EP | 2014877 A2 | 1/2009 |
| EP | 2574905 A1 | 4/2013 |

(Continued)

OTHER PUBLICATIONS

French Search Report for French Application No. FR 1909954, Completed by the French Patent Office, dated May 27, 2020, 9 pages.

*Primary Examiner* — David Z Huang
(74) *Attorney, Agent, or Firm* — Brooks Kushman P.C.

(57) ABSTRACT

A method and a system for monitoring a mechanical system, the mechanical system including a lubrication system provided with a reservoir containing a lubricating liquid, with a lubrication circuit designed to lubricate the mechanical system, as well as with a particle detection device arranged in the lubrication circuit. The detection device makes it possible, in particular, to count the number of particles flowing through the lubrication circuit and/or the flow rate of the particles. Comparing that number or that flow rate with a first threshold makes it possible to determine a risk of damage affecting the mechanical system and to anticipate the maintenance or reinforced monitoring operations that possibly need to be performed.

20 Claims, 2 Drawing Sheets

(51) Int. Cl.
*F16H 57/04* (2010.01)
*G01N 15/06* (2006.01)
*G01N 33/28* (2006.01)
*G08B 21/18* (2006.01)
*F16N 19/00* (2006.01)
*F16N 39/06* (2006.01)

(52) U.S. Cl.
CPC ..... *F16H 57/0405* (2013.01); *G01N 15/0606* (2013.01); *G01N 15/0656* (2013.01); *G01N 33/2888* (2013.01); *G08B 21/182* (2013.01); *B64D 2045/0085* (2013.01); *F16N 19/00* (2013.01); *F16N 39/06* (2013.01); *F16N 2210/08* (2013.01); *G01N 2015/0693* (2013.01)

(58) Field of Classification Search
CPC ....... G01N 33/2888; G01N 2015/0693; G08B 21/182; F16N 39/06; F16N 2210/08
See application file for complete search history.

(56) References Cited

U.S. PATENT DOCUMENTS

| | | |
|---|---|---|
| 2009/0240471 A1 | 9/2009 | Novis |
| 2009/0314064 A1 | 12/2009 | Augros et al. |
| 2013/0332045 A1* | 12/2013 | Uluyol ............... F16N 29/00 701/102 |
| 2016/0266006 A1 | 9/2016 | McKimpson et al. |
| 2017/0248572 A1* | 8/2017 | Byington ........... G01N 33/2888 |
| 2019/0162687 A1* | 5/2019 | Best ..................... F02C 7/06 |

FOREIGN PATENT DOCUMENTS

| | | |
|---|---|---|
| FR | 2508168 A1 | 12/1982 |
| FR | 2927401 A1 | 8/2009 |

\* cited by examiner

METHOD AND A SYSTEM FOR MONITORING A LUBRICATED MECHANICAL SYSTEM

CROSS-REFERENCE TO RELATED APPLICATIONS

This application claims priority to French patent application No. FR 19 09954 filed on Sep. 10, 2019, the disclosure of which is incorporated in its entirety by reference herein.

BACKGROUND OF THE INVENTION

(1) Field of the Invention

The present invention lies in the field of mechanical devices and of mechanical transmissions, and in particular of mechanical transmissions for an aircraft.

The present in relates to a method and a system for monitoring a lubricated mechanical system. This monitoring method and this monitoring system are particularly well suited to monitoring operation of a power transmission main gearbox of a rotary-wing aircraft.

(2) Description of Related Art

A mechanical system generally has moving elements, e.g. rotary elements, such as shafts and bearings, as well as power transmission elements, or indeed elements for reducing or increasing rotation speeds, such as gears and/or gear trains. It is then essential, in order for the mechanical system to operate properly, to lubricate and to cool such rotary elements by means of a lubricating liquid, e.g. oil. Such lubrication is, in general, provided by a lubrication system, and its main functions are to limit wear and overheating of such rotary elements of the mechanical system, and, as a result, to extend their life spans. Without such lubrication, operation of the mechanical system can become rapidly degraded, or indeed impossible.

A lubrication system includes a reservoir or sump that stores and recovers the lubricating liquid. In addition, the lubrication system includes one or more lubrication circuits and at least one flow generator, e.g. a pump, in order to feed lubricating liquid to each lubrication circuit. Each lubrication circuit may include spray nozzles that spray the lubricating liquid over at least the essential rotary and mechanical transmission elements of the mechanical system.

A lubrication circuit may also include at least one cooling device, e.g. a liquid-air heat exchanger, in order to limit or indeed prevent overheating of the lubricating liquid.

Furthermore, while it is operating, the mechanical system can generate particles coming from its various moving elements, e.g. at sets of teeth on the gears and/or gear trains, and at the bearings. Such particles can come from normal wear of the rotary elements. However, they can also appear as a result of degradation or damage of at least one of the rotary or power transmission elements of the mechanical system. The moving elements are often metal elements, e.g. made of steel or of titanium. However, moving elements can also be non-metal elements, e.g. made of ceramic.

In addition, particles can also be generated by components of a lubrication circuit, e.g. by a cooling device.

Those particles can then be entrained into the reservoir of the lubrication system and can flow through each lubrication circuit via the flow generator. Such particles can then, for example, disrupt proper operation of the flow generator and/or obstruct a nozzle, thereby disrupting the spraying of the lubricating liquid that is sprayed by said nozzle, or indeed stopping it.

The presence of such particles in significant quantities can be a sign of the presence of damage to one of the components of the mechanical system and of a risk of forthcoming failure of the mechanical system.

However, such particles can also come from pollution in the lubricating liquid, without the mechanical system or the lubrication system having been degraded or damaged. In addition, other particles, be they metal or non-metal particles, can also be found in the reservoir or flow through each lubrication circuit.

In order to limit or indeed stop the flow of metal or non-metal particles, a lubrication system may include one or more capture devices making it possible firstly to filter the lubricating liquid, and secondly to capture some of said particles.

For example, one or more "mechanical" capture devices are known that can be incorporated into the lubrication system and that make it possible to block certain metal or non-metal particles. Mechanical capture devices are provided with orifices in order to allow the lubricating liquid to pass through them and they prevent particles of dimensions greater than the dimensions of those orifices from exiting from them. Such mechanical capture devices are also commonly referred to as "filtration devices".

A first mechanical capture device is, for example, formed by a strainer and can be arranged upstream from a flow generator, at a suction inlet of a lubrication circuit. The first mechanical filtration device prevents certain particles from penetrating into the lubrication circuit by blocking them in the reservoir.

A second mechanical capture device is, for example, formed by a filter and can be arranged in a lubrication circuit upstream and/or downstream from a cooling device. A second mechanical filtration device arranged upstream from the cooling device thus prevents certain particles from penetrating into the cooling device and possibly accumulating inside said cooling device. A second mechanical filtration device arranged downstream from the cooling device prevents particles generated by said cooling device or previously trapped by said cooling device from moving inside the lubrication circuit.

For example, a third mechanical capture device is, once again, formed by a strainer or indeed by a screen, and can be arranged at the spray nozzles of the lubrication system in order to block the particles that have escaped the preceding mechanical capture devices before spraying the lubricating liquid.

A capture device can also be magnetic and be arranged in the lubrication system in order to capture and to retain only the metal particles that go past nearby, unlike a mechanical capture device that can capture all particles.

For example, magnetic capture devices can be in the form of magnetic plugs or stoppers that can be arranged in the reservoir of a lubrication system. Magnetic plugs can also be arranged in a pipe of a lubrication circuit or indeed at the inlet and/or at the outlet of a cooling device. However, such magnetic plugs can capture only a fraction of the metal particles flowing past nearby, the other metal particles being able to flow freely by. In addition, the non-metal particles are not captured by the magnetic plugs.

A capture device can also be formed by a particle retention region for retaining particles that is situated in the reservoir or indeed in the flow of lubricating liquid. Such a particle retention region has a particular shape making it possible to trap particles, e.g. by gravity or indeed by a centrifugal force generated by the flow of the lubricating liquid.

For example, a retention region can include a cavity arranged at the bottom of a reservoir, particles present in the lubricating liquid accumulating by gravity in said cavity. A retention region can also include an accumulation region and a baffle arranged in the flow of the lubricating liquid enabling at least a fraction of the particles flowing in the lubricating liquid to be trapped in the accumulation region.

A retention region can also have an accumulation region and a specific shape making it possible to generate a current or stream, e.g. a vortex, in the lubricating liquid. The current in the lubricating liquid then makes it possible, e.g. by means of the centrifugal force, to direct a fraction of the particles flowing in the lubricating liquid towards the accumulation region, where they are trapped.

An optionally magnetic plug may be arranged in the cavity or in the accumulation region of the retention region in order to collect the accumulated particles.

Those various capture devices can be inspected during periodic maintenance inspections, in particular in order to recover the captured particles. The particles can be analyzed in order to determine firstly their quantity and their type(s), in particular whether they are metal particles or non-metal particles, and secondly, possibly, their origins, so as to define whether they result from normal wear or else from degradation or damage of a mechanical element of the mechanical system. For example, such degradation or damage may be constituted by abnormal and/or unacceptable wear of a moving element of the mechanical system, by a crack in a moving element, or indeed by breakage of a moving element. Degradation or damage generally requires work to be done rapidly so as to replace the offending element, it being possible for operation of the mechanical system to be degraded or indeed rapidly stopped.

Such scheduled inspections of the capture devices represent a considerable maintenance workload, since the capture devices can be difficult to access. Even so, degradation or damage occurring between two inspections will not be detected before the following inspection and can lead to considerable damage or degradation, or indeed to destruction, of the mechanical system.

In order to mitigate this risk, "signaling" or "electric" magnetic capture devices make it possible firstly to capture metal particles and secondly to detect that a quantity of metal particles greater than a predetermined threshold has been captured, and to generate an alarm accordingly. However, such signaling magnetic capture devices capture only the metal particles that flow past near to the magnetic capture devices, and sometimes require a large quantity of metal particles to be captured in order to trigger an alarm. The mechanical system must then, by way of precaution, be immediately stopped whenever an alarm is triggered, which causes the mission being flown to be stopped immediately and the aircraft to be landed rapidly when it is equipped with the potentially defective mechanical system, and causes the aircraft to be grounded, i.e. taken out of operation, until the mechanical system has been inspected and possibly repaired or changed.

Document FR 2 927 401 discloses an example of a signaling magnetic plug equipping a mechanical system of an aircraft.

Such devices have some advantages. However, the metal particles that are captured can come from pollution in the lubricating liquid, without the mechanical system having been damaged or degraded. Therefore, the mechanical system can be stopped immediately following a false alarm in the presence of pollution in the lubricating liquid while, in actual fact, no mechanical damage or degradation is present.

A particle detection device may also be used in a lubrication system. Such a detection device may also be referred to as an "Oil Debris Monitoring" or "ODM" device. For example, an ODM detection device makes it possible to count the particles going past nearby, and optionally to determine their sizes, their flow rates and/or their masses. The information provided on such detected particles can therefore be incomplete, and the detected particles continue to flow through the lubrication circuit.

An ODM detection device can be inductive and then detects metal particles only. An ODM detection device can be optical or acoustic and then detects all of the particles, be they metal or non-metal particles, that go past nearby as well as any air bubbles present in the lubricating liquid.

An ODM detection device may also use a plurality of different technologies and, for example, be firstly inductive and secondly optical or acoustic. In which case, the ODM detection device can thus detect all of the particles going past nearby and identify not only the metal particles, but also the non-metal particles.

In addition, an ODM detection device can be combined with a capture device, thereby making possible firstly to detect, at least partially, the particles going past near to the ODM detection device, and secondly to capture, also at least partially, the particles going past near to the ODM detection device, the captured particles being metal or of any other type depending on the capture technology used.

Documents US 2009/0240471, US 2016/0266006, EP 2 014 877 and EP 2 574 905 are known that describe the use of such a particle detection device. Document US 2009/0240471 describes a detection system for detecting failure of a mechanical system, e.g. a gas turbine engine. That detection system includes a plurality of sensors, in particular a device for analyzing vibration and a device for detecting, without capturing, the quantity and the size of the particles in suspension in the lubricating liquid. Document US 2016/0266006 discloses a monitoring system for monitoring a gearbox of a vehicle. That monitoring system uses a device for detecting, without capturing, the quantity and the size of the particles in suspension in the lubricating liquid of that gearbox. For example, that detection device may be optical or indeed magnetic.

Document EP 2 014 877 discloses a system for monitoring a gas turbine engine. That system uses a plurality of devices for capturing metal and non-metal particles, such as a filter or a magnetic plug, as well as at least one device for detecting metal and non-metal particles flowing with a lubricating liquid.

Finally, Document EP 2 574 905 discloses a system for monitoring particles that can pollute a lubrication circuit or indeed a hydraulic system. That monitoring system includes an optical device for detecting particles that makes it possible to measure the sizes and the quantities of particles flowing through the lubrication circuit or indeed in the hydraulic system.

BRIEF SUMMARY OF THE INVENTION

An object of the present invention is thus to propose a method and a system for monitoring a lubricated mechanical system that aims to overcome the above-mentioned limitations, by anticipating the risks of damage occurring to the mechanical system while also limiting the risks of triggering false alarms. An object of the present invention is thus to improve detection of damage to the mechanical system and to optimize the maintenance operations on said mechanical system accordingly.

The present invention provides a method of monitoring a lubricated mechanical system.

A mechanical system generally has moving elements, or indeed rotary elements, such as rotary shafts and bearings, as well as power transmission elements and elements for reducing or increasing rotation speeds. For example, a mechanical system makes it possible to transmit mechanical power from a power plant of the vehicle to propulsion means for propelling the vehicle.

In order for the mechanical system to operate properly, and, where applicable, in order for a vehicle including such a mechanical system to operate properly, it is then essential to lubricate and to cool the rotary elements and the power transmission or gearbox elements of the mechanical system with a lubricating liquid, e.g. oil. To this end, the mechanical system includes a lubrication system provided with:

at least one reservoir containing a lubricating liquid;

at least one lubrication circuit through which the lubricating liquid flows and which is designed to lubricate the mechanical system, said at least one lubrication circuit including pipes through which the lubricating liquid flows;

at least one flow generator for generating a flow of the lubricating liquid and making it possible to feed at least one lubrication circuit with the lubricating liquid; and at least one particle capture device.

Each lubrication circuit then conveys the lubricating liquid to the elements of the mechanical system that are to be lubricated and may include spray nozzles in order to spray the lubricating liquid onto those elements. The reservoir of the lubrication system is, for example, constituted by a casing of the mechanical system.

The monitoring method of the invention comprises the following steps:

measuring at least one first characteristic of detected particles flowing through at least one pipe of a lubrication circuit;

comparing at least one first characteristic with a first threshold;

collecting particles captured by said at least one capture device if at least one first threshold is exceeded;

measuring at least one second characteristic of the captured particles;

comparing at least one second characteristic of the captured particles with a second threshold; and performing maintenance on the mechanical system if at least one second threshold is exceeded.

The method of the invention makes it possible firstly to identify a potential risk of damage occurring on the mechanical system by measuring and by comparing at least one first characteristic of detected particles flowing through a pipe of a lubrication circuit without stopping the mechanical system, and then to adapt advantageously the maintenance operation that is possibly to be implemented so that that risk can be confirmed or not confirmed. In addition, false alarms are also limited by using the method of the invention.

In this way, disassembling the mechanical system that takes said mechanical system and possibly the vehicle including said mechanical system out of operation, is thus performed only in the event of established damage to the mechanical system. The method of the invention therefore makes it possible to optimize the maintenance operations on the mechanical system in terms both of cost and of time for which the mechanical system is taken out of operation.

Measuring at least one first characteristic of said particles is performed by at least one particle detection device. Said at least one detection device is preferably arranged in the flow of the lubricating liquid of a lubrication circuit, typically in a pipe of at least one lubrication circuit. This detection device may be optical, acoustic, or inductive, and is, for example, of the ODM type. For example, a particle detection device is arranged in a pipe of each lubrication circuit of the lubrication system.

Said particle detection device may make it possible only to detect particles, without capturing or blocking said particles.

Said particle detection device may be combined with a capture device making it possible firstly to detect particles going past near to the detection device, and secondly to capture at least some of the particles going past nearby, it being possible for the particles that are captured to be metal or to be of any other type depending on the capture technology used.

In addition, each detection device also makes it possible to characterize the detected particles. The detected particles may thus be characterized by a single first characteristic, typically the number of detected particles, or indeed by a plurality of first characteristics. Each first characteristic may be chosen from among the number of detected particles, the flow rate of detected particles flowing through the lubrication circuit and near to the detection device, the size of each detected particle, or indeed the maximum size of a particle from among the detected particles, and the mass of each detected particle or indeed the maximum mass of a particle from among the detected particles.

For example, the size of a particle is proportional to the amplitude of an electrical signal received by the detection device. This electrical signal is then processed by a computer associated with the detection device, or indeed incorporated into an electronic system of the mechanical system, typically the avionics system of an aircraft when the mechanical system is on board an aircraft, in order to determine the size of each detected particle using a conversion table. For example, the conversion table may be established during preliminary calibration testing of the detection device.

Then, at least one first characteristic of the detected particles is compared with a corresponding first threshold, e.g. by a computer. For example, this computer may be incorporated into the mechanical system or indeed, where applicable, into the vehicle including said mechanical system. For example, said computer may be incorporated into an avionics system of an aircraft including the mechanical system.

The computer may comprise at least one processor and at least one memory, at least one integrated circuit, and at least one programmable system or indeed at least one logic circuit, these examples not limiting the scope given to the expression "computer". The computer may be a computer dedicated to performing the method of the invention, or it may be a shared computer having multiple functions. For example, the memory may store one or more first thresholds, each corresponding to a respective, distinct first characteristic.

When a plurality of first characteristics of detected particles are determined, each first characteristic is preferably compared independently of the other first characteristics with a first threshold specific to said first characteristic.

However, a combination of at least two first characteristics of detected particles may also be compared with a first threshold corresponding to such a combination.

Following that comparison, the particles captured by said at least one capture device are collected if at least one first threshold is exceeded. A first threshold is exceeded whenever a first characteristic is greater than the corresponding first threshold. For example, a first threshold is exceeded whenever the number of detected particles is greater than a first threshold, e.g. equal to 30. A first threshold is also exceeded whenever the flow rate of detected particles flowing through the lubrication circuit is greater than a first threshold, e.g. equal to 10 particles per hour, or indeed whenever the maximum size of the detected particles is greater than a first threshold, e.g. equal to at least one particle greater than 800 micrometers (800 μm). The number of detected particles is equal to the cumulative number of particles detected since that number was initialized, as it is generally during a major maintenance operation on the mechanical system.

If a combination of at least two first characteristics of detected particles is used, the captured particles are collected if such a combination is greater than the first threshold corresponding to said combination.

A capture device may be a magnetic plug, a filter, a strainer, or indeed a screen arranged on the lubrication system. A capture device may also be constituted by a particle retention region for retaining particles that is situated in the reservoir or indeed in the flow of the lubricating liquid.

Collecting the particles consists firstly in inspecting one or more capture devices, and, in the event of presence of particles captured by at least one capture device, said captured particles are collected, namely removed from said at least one capture device, for analysis.

In addition, an alarm may be triggered if at least one first threshold is exceeded by a first characteristic of the detected particles. Such an alarm may be triggered whenever at least one first threshold is exceeded. However, such an alarm may be triggered if at least one first threshold is exceeded and after said mechanical system stops.

A first threshold being exceeded indicates that a risk of damage to the mechanical system exists and should be confirmed or not confirmed by performing an additional analysis of particles captured in the lubrication system. No damage is then established yet, and operation of the mechanical system is not in danger. There is therefore no urgency for stopping the mechanical system, and triggering of an alarm can be deferred until the mechanical system is stopped, in particular for an aircraft in flight. The mechanical system or indeed the vehicle including said mechanical system includes an alarm device in order to trigger the alarm. The alarm may be audible or visual, for example, in order to inform an operative or a crew, when the mechanical system is on board an aircraft, of the risk.

In addition, the mechanical system may include a signaling magnetic capture device associated with an alarm device in order to warn the operative or the crew whenever a quantity of particles that is greater than a threshold is captured, such a quantity of particles being indicative of a risk of presence of damage to the mechanical system.

Since an alarm triggered following at least one first threshold being exceeded by a first characteristic of the detected particles is triggered before an alarm is triggered by the signaling magnetic capture device, the method of the invention advantageously makes it possible to anticipate detection of a possible risk of damage and optionally to act through an inspection or a maintenance operation on the mechanical system before damage to the mechanical system actually happens or indeed while such damage is not yet too substantial.

Following collection of the particles captured by at least one capture device of the lubrication system of the mechanical system, an analysis of said particles is performed. Firstly, at least one second characteristic of the captured particles is measured. This measuring of at least one second characteristic of the captured particles may be performed manually, typically firstly visually and then supplemented by an analysis in the laboratory. This measuring of at least one second characteristic of the captured particles can thus be performed totally automatically.

Each second characteristic may be chosen from among the number of captured particles, the size of each captured particle, or indeed the maximum size of a particle from among the captured particles, the mass of each captured particle, or indeed the maximum mass of a particle from among the captured particles, and the material and the morphology of the captured particles.

The morphology of a particle makes it possible to characterize the shape of the particle. In particular, the morphology makes it possible to distinguish between a particle that is formed by swarf coming from machining of an element of the mechanical system and that is therefore not indicative of damage to the element, and a particle that has subsequently flaked off, e.g. due to material of an element of the mechanical system being torn off, and that is representative of damage.

Then, at least one second characteristic of the captured particles is compared with a second threshold, e.g. by a dedicated computer. One or more second thresholds corresponding to respective ones of the distinct second characteristics may be stored in the memory of the computer.

When a plurality of second characteristics of captured particles are determined, each second characteristic is preferably compared independently from the other second characteristics with a second threshold specific to said second characteristic.

However, a combination of at least two second characteristics of captured particles may also be compared with a second threshold corresponding to such a combination. In particular, material and morphology are second characteristics used in combination with number, size and/or mass.

Following this comparison and if at least one second threshold is exceeded by a second characteristic, a maintenance operation is performed on the mechanical system. If a second threshold is exceeded, i.e. if a second characteristic is greater than the corresponding second threshold, the captured particles confirm that a risk of damage to at least one rotary element or mechanical transmission element of the mechanical system exists. A maintenance operation is thus necessary in order to disassemble the mechanical system at least in part, in order to identify the damage done, and in order to repair the mechanical system.

For example, a second thresh old is exceeded whenever the number of captured particles is greater than a second threshold, e.g. equal to 10, or indeed whenever the maximum size of the captured particles is greater than a second threshold, e.g. equal to 800 micrometers (800 μm).

The method may further have one or more of the following characteristics, taken individually or in combination.

In one aspect, if each second characteristic of the captured particles is less than the corresponding second threshold and at least one of the second characteristics is greater than a third threshold, the third threshold being less than the second threshold, the method may further comprise the following additional steps:

analyzing said at least one first characteristic of the detected particles so as to identify whether the lubricating liquid is polluted;

cleaning the mechanical system if pollution of the lubricating liquid is identified; and scheduling regular collections of the particles captured by said at least one capture device if no pollution of the lubricating liquid is identified.

The presence of the particles in one or more lubrication circuits or indeed in the reservoir of the lubrication system can be due to pollution of the lubricating liquid rather than to damage to an element of the mechanical system. Therefore, the method of the invention makes it possible, during this analysis and on the basis of the measurements of said at least one first characteristic of the detected particles, to identify whether the lubricating liquid is polluted, thereby advantageously avoiding launching an unnecessary major maintenance operation following such pollution of the lubricating liquid. The mechanical system and each lubrication circuit can then be cleaned in order to remove the pollution of the lubricating liquid.

Conversely, if no significant pollution of the lubricating liquid is identified, a risk of damage to at least one rotary or mechanical transmission element of the mechanical system remains possible, even though it is not yet established. Therefore, reinforced monitoring of the mechanical system is launched in order to monitor said risk of damage closely. This reinforced monitoring includes, in particular, scheduling regular collections and analyses of the particles captured by at least one capture device of the lubrication system of the mechanical system.

This scheduling of regular collections of captured particles is performed with intervals between inspections that are short compared with a usual preventive maintenance procedure in order to anticipate detection of damage or degradation to the mechanical system.

During the step of analyzing said at least one first characteristic, a variation over time of a first characteristic of the detected particles is analyzed. Thus, the presence of pollution of the lubricating liquid is identified if said variation over time of a first characteristic of the detected particles includes a first increase over a first time interval, and then a substantially constant plateau over a second time interval. The presence of pollution of the lubricating liquid is also detected if the variation over time of a first characteristic of the detected particles includes a plurality of increases and a plurality of substantially constant plateaus in succession, thereby forming a curve in the shape of a "staircase", i.e. in the shape of a step curve.

The presence of pollution of the lubricating liquid is also identified if said variation over time of a first characteristic of the detected metal particles includes a first increase over a first time interval, and then a second increase less than said first increase over a second time interval, the second time interval immediately following the first time interval. In this way, said variation over time of a first characteristic of the detected metal particles is an increasing curve with at least one change of slope, said slope decreasing with increasing time. For example, the first characteristic of the detected metal particles varies over time in the form of a logarithmic curve.

Conversely, no pollution of the lubricating liquid is identified if said variation over time of a first characteristic of the detected particles increases constantly and in linear manner.

Similarly, no pollution of the lubricating liquid is identified if said variation over time of a first characteristic of the detected particles includes a first increase over a first time interval, and then a second increase greater than the first increase over a second time interval. In this way, said variation over time of a first characteristic of the detected metal particles is an increasing curve with at least one change of slope, said slope increasing with increasing time.

For example, the first characteristic of the detected particles varies over time in the form of an exponential curve or indeed of a parabolic curve.

In both of these situations, a risk of presence of damage or of degradation to at least one element of the mechanical system remains possible and the reinforced monitoring of the mechanical system should be launched.

In addition, said at least one characteristic may be analyzed independently of the steps of collecting the captured particles, and of measuring and of comparing at least one second characteristic, after the step of comparing at least one first characteristic of the particles with a first threshold and if at least one first threshold is exceeded.

In this way, the step of analyzing said at least one first characteristic advantageously makes it possible to identify the origin of the detected particles and to distinguish between particles coming from damage to a moving element or the mechanical system and pollution of the lubricating liquid, without doing work on the mechanical system and without stopping or disasembling said mechanical system. This detection step can thus make it possible to adapt the maintenance operation to be performed as a function of the origin of said particles, and also to limit the risk of false alarm, without the steps of collecting the captured particles, and of measuring and of comparing at least one second characteristic being performed.

This step of analyzing said at least one first characteristic may be performed by the computer included in the mechanical system or indeed in the vehicle including the mechanical system, optionally while the mechanical system is operating. In this way, as soon as the mechanical system is stopped, any cleaning of the mechanical system can be launched rapidly if pollution of the lubricating liquid is identified.

When the mechanical system equips an aircraft, the method of the invention may further comprise a step of transmitting said at least one first characteristic of the particles detected during a flight to a base on the ground and equipped with a computer in order to perform the step of analyzing said at least one first characteristic. In which case, detecting of any pollution of the lubricating liquid can be performed before the end of the flight of the aircraft and any cleaning of the mechanical system can be launched rapidly if pollution of the lubricating liquid is identified.

The step of transmitting said at least one first characteristic of the detected particles to a base on the ground may also be performed once the aircraft is on the ground.

In another aspect of the invention, the step of measuring at least one first characteristic of detected particles flowing through at least one pipe of a lubrication circuit may be limited to the metal particles that are detected.

Indeed, when the rotary elements and the power transmission elements of the mechanical system are all made of metal, any non-metallic particles that might be detected are not indicative of damage to those elements and can then lead to a non-existent risk of damage being detected. Measuring at least one first characteristic of only the detected metal particles makes it possible to mitigate this risk.

In this situation, the particle detection device may detect the metal particles only or indeed identify the metal particles from among the detected particles. For example, the detection device may be inductive and then detects metal particles only. The detection device may thus also use a plurality of technologies and, for example, be firstly inductive and secondly optical or acoustic in order to detect all of the particles going past nearby and in order to identify the metal particles from among said particles.

Therefore, the step of comparing at least one said first characteristic with a first threshold is also limited to each first characteristic of the detected metal particles in order to identify a risk of damage to a metal element of the mechanical system.

In addition, the step of analyzing said at least one first characteristic of the detected particles in order to identify whether the lubricating liquid is polluted is also made only on the captured metal particles.

Conversely, when the mechanical system includes metal elements and non-metal elements, e.g. elements made of ceramic, it is preferable to detect all of the particles, both the metal ones and the non-metal ones, that are flowing with the lubricating liquid, and to compare the first characteristics of said detected metal and non-metal particles with a first threshold.

In another aspect of the invention, the step of collecting the particles captured by said at least one capture device if at least one first threshold is exceeded may also be limited to the metal particles for the same reasons as above, namely when all of the rotary elements and all of the power transmission elements of the mechanical system are made of metal.

A capture device may be a magnetic plug making it possible to capture only the metal particles, which are easy to collect once the magnetic plug is removed.

A capture device may be a filter, a strainer, a screen, or a retention region, making it possible to capture particles of any type, i.e. metal particles and non-metal particles. The collected particles are then sorted in order to identify and isolate the captured metal particles. This sorting may, for example, be performed by means of a magnetic device.

Therefore, the step of measuring at least one second characteristic of the captured particles and the step of comparing at least one second characteristic of the captured particles with a second threshold are also limited to the metal particles that are captured, in order to enable the risk of damage to a metal element of the mechanical system to be confirmed or not confirmed.

Conversely, when the mechanical system includes metal elements and non-metal elements, e.g. elements made of ceramic, it is preferable to collect all of the particles, both the metal ones and the non-metal ones, that are captured by each capture device, and to compare the second characteristics of said captured metal and non-metal particles with a second threshold.

The present invention also provides a monitoring system for monitoring a lubricated mechanical system, the monitoring system including a lubrication system for lubricating the mechanical system, the lubrication system being provided with:

at least one reservoir containing a lubricating liquid;

at least one lubrication circuit through which the lubricating liquid flows and which is designed to lubricate the mechanical system, said at least one lubrication circuit including spray nozzles, and pipes through which the lubricating liquid flows;

at least one flow generator for generating a flow of the lubricating liquid and making it possible to feed at least one lubrication circuit with the lubricating liquid; and at least one particle capture device.

The monitoring system further includes at least one particle detection device arranged in at least one lubrication circuit, as well as at least one computer and an alarm device, the monitoring system being configured to implement the above-described method of monitoring a lubricated mechanical system.

A particle capture device may include at least one magnetic plug or at least one signaling magnetic plug or indeed a filter, a strainer, a screen, or a retention region.

The lubrication system may also include at least one device that can trap the metal and non-metal particles, e.g. a filtration device, such as a filter, a strainer and a screen, or indeed a heat exchanger device. The detection device is preferably arranged downstream from the flow generator and upstream from such a device that can, trap the particles in order to limit the risk of the particles being trapped by such a device.

For example, a particle detection device may be an inductive, acoustic, or optical device. A particle detection device may be a device of the ODM type.

The monitoring method and the monitoring system of the invention may also be applied to a mechanical system lubricated by splashing, at least one detection device being, for example, arranged in a place through which the lubricating liquid flows in order to detect the first characteristics of the particles flowing with the lubricating liquid.

The present invention also provides a mechanical system including:

rotary elements;

elements for transmitting power and for reducing or increasing rotation speed; and a monitoring system for monitoring a lubricated mechanical system as described above.

For example, the mechanical system may be a power transmission main gearbox of a rotary-wing aircraft.

The present invention finally provides an aircraft including such a mechanical system.

BRIEF DESCRIPTION OF THE DRAWINGS

The invention and its advantages appear in greater detail from the following description of examples given by way of illustration with reference to the accompanying figures, in which.

DETAILED DESCRIPTION OF THE INVENTION

Elements present in more than one of the figures are given the same references in each of them.

Figure 1:
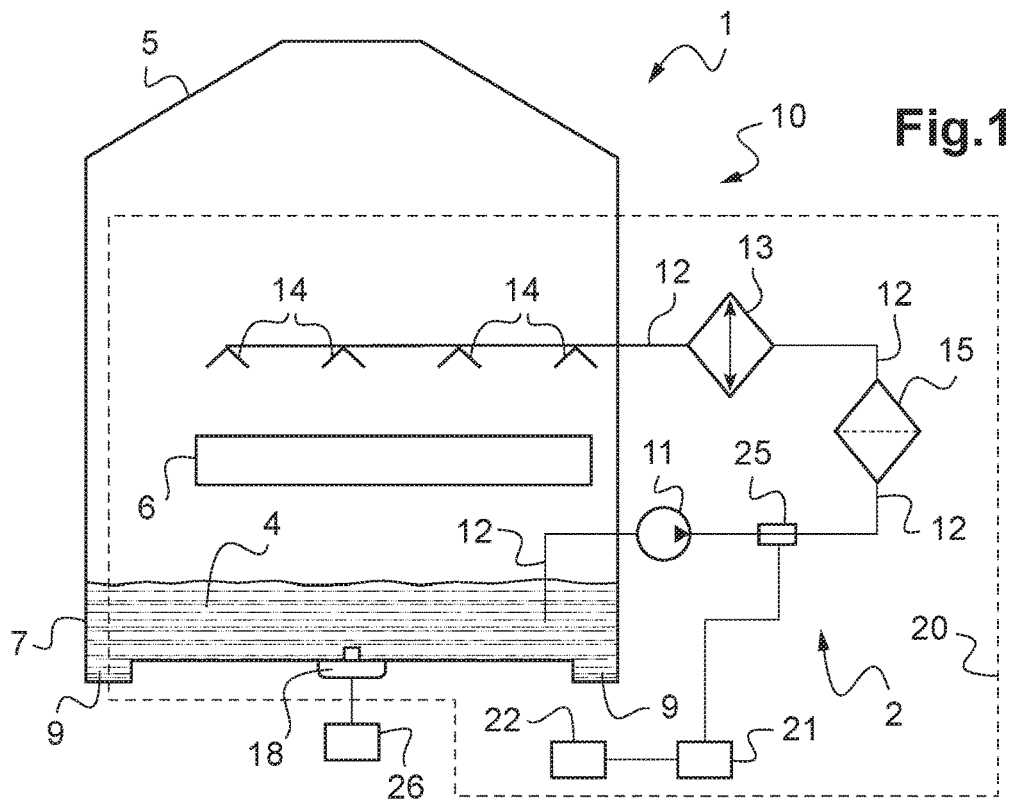
FIGS. 1 and 2 show examples of mechanical systems.
Figure 2:
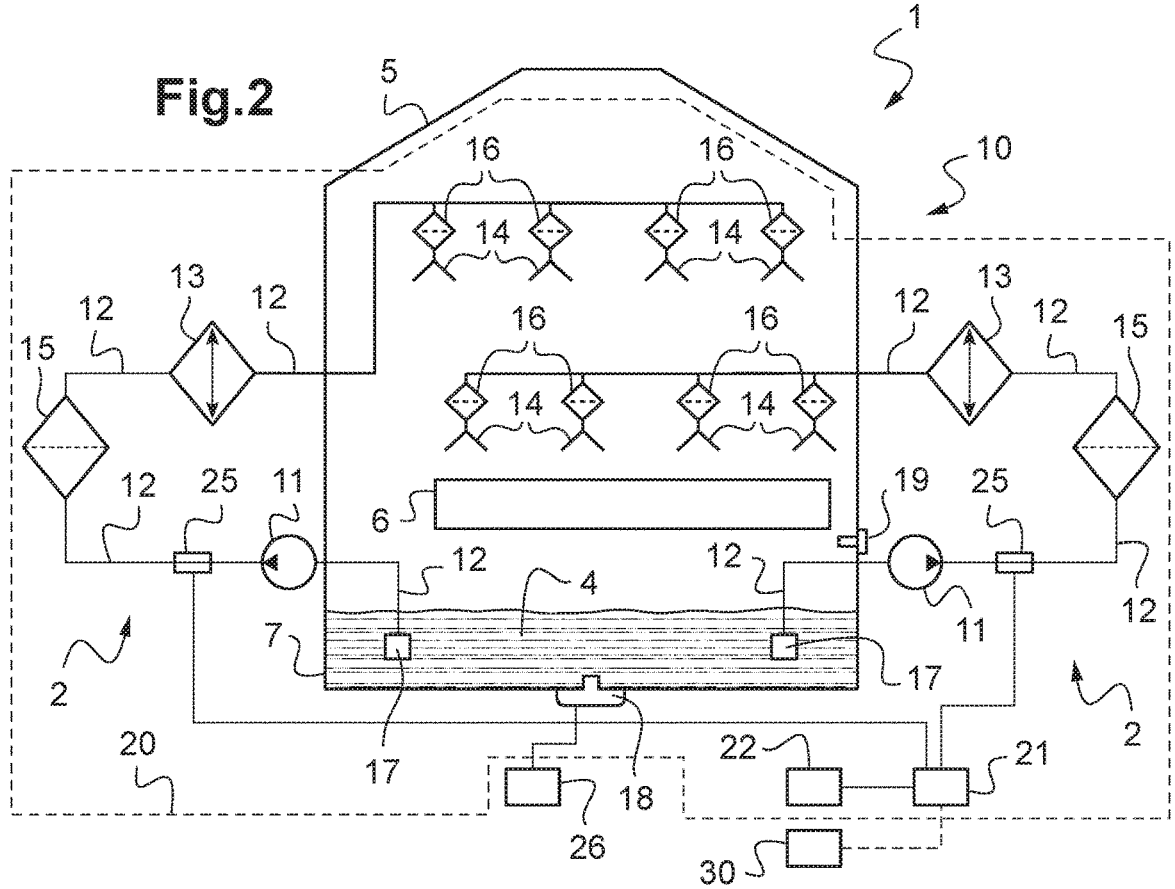

FIGS. 1 and 2 show a mechanical system 1 including a monitoring system 20 for monitoring said mechanical system 1. This mechanical system 1 includes, in particular, a casing 5 and moving mechanical elements 6, in particular rotary elements, such as shafts and bearings, as well as power transmission elements, and elements for reducing or increasing rotation speeds, such as gears and/or gear trains. For example, this mechanical system 1 is a power transmission main gearbox equipping a rotary-wing aircraft.

The monitoring system 20 includes a lubrication system 10, at least one particle detection device 25 arranged in the lubrication system 10, a computer 21, and an alarm device 22.

In the first example of the mechanical system 1, shown in FIG. 1, the lubrication system 10 includes a single lubrication circuit 2, while the second example of the mechanical system 1, shown in FIG. 2, includes two identical lubrication circuits 2. Each lubrication circuit 2 makes it possible simultaneously to lubricate and to cool the moving mechanical elements 6 of the mechanical system 1.

In a manner that is common to these two examples, the lubrication system 10 includes a reservoir 7 formed by a lower portion of the casing 5 of the mechanical system 1 and containing a lubricating liquid 4, such as oil, and a magnetic plug 18 arranged at the bottom of said reservoir 7. Each lubrication circuit 2 of the lubrication system 10 also includes a flow generator 11, such as a pump, a cooling device 13 formed by a heat exchanger, spray nozzles 14, at least one particle capture device 15-19, and pipes 12 interconnecting these various components.

A particle detection device 25 of the monitoring system 20 is also arranged on each lubrication circuit 2 on a duct 12 positioned downstream from the flow generator 11 and upstream from a capture device 15.

The flow generator 11 makes it possible to suck lubricating liquid 4 from the reservoir 7 and to feed said lubricating liquid to each lubrication circuit 2 until it is sprayed onto the moving mechanical elements 6 of the mechanical system 1 via the spray nozzles 14. The cooling device 13 makes it possible to cool the lubricating liquid 4 before it reaches the spray nozzles 14. The cooling device 13 can also temporarily or indeed permanently trap the metal or non-metal particles flowing through the cooling device 13. Some of said particles can subsequently be randomly fed back into the lubrication circuit 2.

Each capture device 15-19 is arranged on a lubrication circuit 2 in order to capture certain particles flowing with the lubricating liquid 4 so as to limit flowing of them through each lubrication circuit 2. A capture device 15-17 may be a mechanical capture device provided with orifices and making it possible to block certain metal or non-metal particles having dimensions greater than or equal to the dimensions of said orifices. A capture device 18, 19 may also be magnetic and be arranged in the lubrication system 4 in order to capture and to retain only the metal particles that go past nearby.

In the example shown in FIG. 1, the single lubrication circuit 2 includes a mechanical capture device 15 formed by a filtration device, e.g. a filter, arranged downstream from the detection device 25 and upstream from the cooling device 13, as well as a magnetic capture device 18 formed by a signaling magnetic plug arranged in the bottom of the reservoir 7. This magnetic capture device 18 is connected to a secondary alarm device 26 that can trigger an alarm whenever a predetermined quantity of metal particles has been captured by the magnetic capture device 18.

An additional capture device 9 is arranged in the reservoir 7. This additional capture device 9 constitutes a particle retention region and comprises two cavities arranged at the bottom of the reservoir 7 and making it possible to trap metal or non-metal particles by gravity. A plug or stopper (not shown in FIG. 1) may be arranged in each cavity for the purpose of collecting the accumulated particles.

In the example shown in FIG. 2, each lubrication circuit 2 includes a plurality of mechanical capture devices 15-17 and two magnetic capture devices 18-19. A first mechanical capture device 17 is, for example, a strainer that is arranged in the reservoir 7, at the end of a pipe 12, namely upstream from the flow generator 11, blocking certain particles and preventing them from entering the lubrication circuit 2. For example, a second mechanical capture device 15 may be constituted by a filter arranged downstream from the detection device 25 and upstream from the cooling device 13. For example, third mechanical capture devices 15 may be constituted by strainers arranged downstream from the cooling device 13 and upstream from respective ones of the spray nozzles 14. In this way, each third capture device 15 protects a spray nozzle 14 while limiting the risk that one or more particles come to obstruct the spray nozzle 14 at least in part.

The two magnetic capture devices 18-19 have a signaling magnetic plug 18 that is identical to the one in the example of FIG. 1, arranged in the bottom of the reservoir 7, and connected to a secondary alarm device 26, as well as a magnetic plug 19 arranged in a wall of the casing 5, near to moving mechanical elements 6. Each magnetic plug 18, 19 makes it possible to capture the metal particles that are situated or that are moving near to it.

The monitoring system 20 makes it possible to monitor the mechanical system 1 by means of each detection device 25 firstly by detecting particles flowing through each lubrication circuit 2 and going past near to the detection device 25, and by simultaneously measuring at least one first characteristic of said detected particles. Then, said at least one first characteristic or the detected particles may be analyzed in order to identify any risk of occurrence of damage or degradation of at least one moving mechanical element 6 of the mechanical system 1.

To this end, the monitoring system 20 may implement a monitoring method 20 for monitoring the mechanical system 1, which method includes the following steps.

Firstly, a step of measuring at least one first characteristic of the particles detected by the detection device 25 is performed. The detection device 25 may be optical or acoustic in order to detect and to measure the metal or non-metal particles flowing with the lubricating liquid 4 and going past near to the detection device 25. The detection device 25 may also be inductive in order to detect and to measure only the metal particles flowing with the lubricating liquid 4 and going past near to the detection device 25. Each first characteristic of the detected particles is representative of a cumulative quantity of particles going past near to the detection device 25.

Then, a step of comparing at least one first characteristic of the particles detected by the detection device 25 with a first threshold is performed by means of the computer 21. For example, a first characteristic of the detected particles may be the number of detected particles, the flow rate of the particles, or the maximum size from among the sizes of the detected particles. Each first characteristic of the detected particles is representative of a cumulative quantity of particles captured by one or more capture devices 15-19. For example, a first threshold corresponding to each first characteristic may be stored in a memory of the computer 21.

After this comparison step and if at least one threshold is exceeded, a step of collecting particles captured by at least one capture device 15-19, or indeed by each capture device 15-19 of a lubrication circuit 2, is performed. Each first threshold is defined to detect such a risk before an alarm is triggered by means of the secondary alarm device 26 connected to the signaling magnetic plug 18.

After inspecting one or more capture devices 15-19, collecting the particles consists in collecting the particles captured by means of at least one capture device 15-19. In this way, the captured particles are removed from said at least one capture device 15-19 for analysis. If only the metal particles captured are to be analyzed, it is necessary to sort the metal particles from the non-metal particles captured by the capture devices 15-17, that sorting being, for example, performed by means of a magnetic device.

Then, a step of measuring said at least one second characteristic of the captured particles is performed by an appropriate device. A second characteristic may be the number and/or the size of the captured particles. As regards the size of the captured particles, the measurement step may be performed manually, e.g. via a graduated precision magnifying glass, or indeed automatically. Each second characteristic of the captured particles is indicative of a cumulative quantity of particles captured by one or more capture devices 15-19.

A step of comparing at least one second characteristic of the captured particles with a second threshold may then be performed by means of a dedicated computer. For example, a second threshold corresponding to each second characteristic may be stored in a memory of the computer 21.

Depending on this comparison, a risk of damage or degradation of a mechanical element 6 of the mechanical system 1 can be identified and a maintenance operation can possibly be performed on the mechanical system 1 so that the presence of said risk of damage or degradation can be confirmed or not confirmed. In this example, whenever a second characteristic is greater than a second threshold, a step of carrying out maintenance on the mechanical system 1 is performed.

The value of a second threshold may be determined by testing, or indeed by feedback from experience. It is known that captured particles of large dimensions are generally indicative of the presence of damage or degradation of the mechanical system, as is a large number of captured particles.

In addition, an alarm may also be triggered by means of the alarm device 22 in order to warn an operative that a first threshold is exceeded and that it is necessary to collect particles captured by one or more capture devices 15-19. This alarm may be triggered whenever a first threshold is exceeded or indeed after the mechanical system has been stopped following the first threshold being exceeded.

Furthermore, comparing at least one first characteristic with a first threshold has made it possible to identify a risk of damage or degradation of a mechanical element 6 of the mechanical system 1 and comparing at least one second characteristic with a second threshold can make it possible to assess whether or not occurrence of such damage or degradation can be established. However, the measurement of said at least one first characteristic may be a first sign that such damage or degradation, of a mechanical element 6 of the mechanical system 1 is in preparation, or it may be consequent upon pollution of the lubricating liquid. A step of analyzing said at least one first characteristic of the detected particles can then make it possible to identify whether pollution of the lubricating liquid 4 is possibly the cause of the measurement of the first characteristic being greater than the first threshold.

Such an analysis step may be performed directly by the computer 21 of the monitoring system 20. Such an analysis step may also be performed outside the monitoring system 20, e.g. by a remote device 30. In which case, the measurement of said at least one first characteristic of the detected particles has to be transferred to the remote device 30, e.g. via a wireless link. The monitoring method 20 for monitoring the mechanical system 1 may then include a step of transmitting said at least one first characteristic of the detected particles to the remote device 30.

When the mechanical system 1 equips an aircraft, the remote device 30 is, for example, a base on the ground, thereby making it possible not to use the computer 21 of the monitoring system 20 for this analysis, in particular if said computer 21 is shared with other devices of the aircraft.

When the mechanical system 1 equips an aircraft, the remote device 30 can also make it possible only to view the curves coming from the analysis step, the aircraft being, for example, still in flight or having landed on the ground. The analysis is then performed by a computer 21 on board the aircraft, e.g. a computer 21 incorporated into the avionics system of the aircraft.

For example, this analysis step may be performed following the comparison of at least one second characteristic of the captured particles with a second threshold if at the same time each second characteristic is less than the second threshold and at least one second characteristic is greater than a third threshold. The third threshold is less than the second threshold.

This analysis step may also be performed after the step of comparing at least one first characteristic of the detected particles with a first threshold and whenever a first threshold is exceeded.

In any event, during this analysis step, pollution of the lubricating liquid 4 may be identified on the basis of the measurement of at least one first characteristic.

Figure 3:
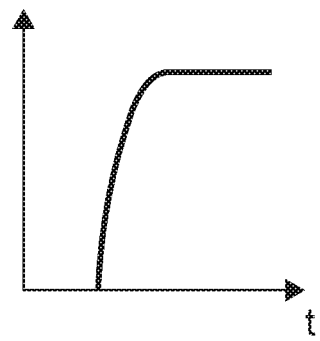
FIGS. 3 to 7 show curves representing variations in a first characteristic of detected particles.

The presence of pollution of the lubricating liquid may be identified if variation over time of a first characteristic of the detected particles includes a first increase over a first time interval, then a substantially constant plateau over a second time interval, as shown in FIG. 3, the second time interval following the first time interval.

Figure 4:
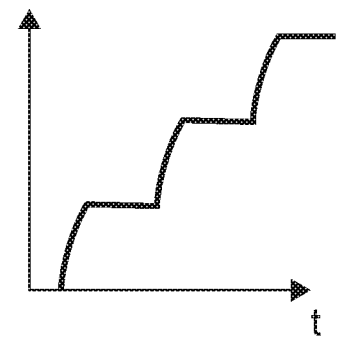

A variation over time of a first characteristic of the detected particles may also be representative of pollution if a plurality of increases and of substantially constant plateaus succeed one another, as shown in FIG. 4. Such a variation thus takes the characteristic shape of a staircase, i.e. of a step curve.

Figure 5:
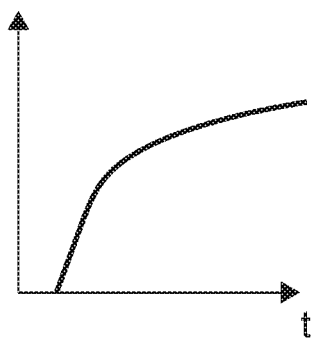

The presence of pollution of the lubricating liquid may also be identified if variation over time of a first characteristic of the detected metal particles includes a first increase over a first time interval, then a second increase less than said first increase over a second time interval, as shown in FIG. 5, the second time interval following the first time interval.

Conversely, no pollution of the lubricating liquid is identified when a variation over time of a first characteristic of the detected particles constantly increases in linear manner, as shown in FIG. 5.

Figure 6:
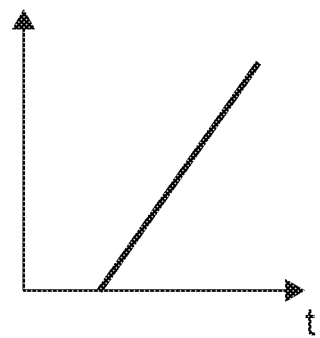
Figure 7:
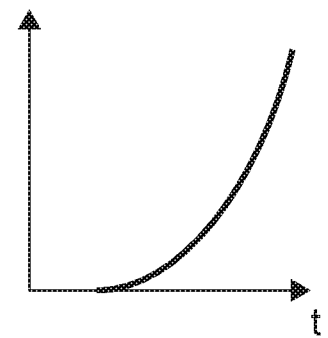

Similarly, no pollution of the lubricating liquid is identified when a variation over time of a first characteristic of the detected particles includes a first increase over a first time interval, then a second increase greater than the first increase over a second time interval, as shown in FIG. 6. For example, such a variation over time of a first characteristic may be in the shape of a parabolic curve or of an exponential curve.

Following this analysis step, a step of cleaning the mechanical system 1 may be performed if pollution of the lubricating liquid 4 is identified, in particular in order to remove said pollution.

Otherwise if no pollution of the lubricating liquid is identified, a risk of presence of damage or degradation of at least one element of the mechanical system exists and a step of scheduling regular collections of the particles captured by at least one capture device 15-19 may be implemented. In this way, reinforced monitoring of the mechanical system is provided in order to monitor the presence or possible occurrence of damage or degradation of a mechanical element 6.

Naturally, the present invention may be subjected to numerous variations as to its implementation. Although several implementations and embodiments are described above, it should readily be understood that it is not conceivable to identify exhaustively all possible implementations and embodiments. It is naturally possible to envisage replacing any of the means described by equivalent means without going beyond the ambit of the present invention.

What is claimed is:

1. A method of monitoring a mechanical system, the mechanical system including a lubrication system provided with:
   at least one reservoir containing a lubricating liquid;
   at least one lubrication circuit through which the lubricating liquid flows and which is designed to lubricate the mechanical system, the lubrication circuit(s) including pipes through which the lubricating liquid flows;
   at least one flow generator for generating a flow of the lubricating liquid and making it possible to feed at least one lubrication circuit with the lubricating liquid; and
   at least one particle capture device;
   wherein the method comprises the following steps:
   measuring at least one first characteristic of detected particles flowing through at least one pipe of a lubrication circuit performed by at least one particle detection device;
   comparing at least one first characteristic of the detected particles with a first threshold;
   collecting particles captured by the capture device(s) if at least one first threshold is exceeded;
   measuring at least one second characteristic of the captured particles;
   comparing at least one second characteristic of the captured particles with a second threshold; and
   performing maintenance on the mechanical system if at least one second threshold is exceeded,
   wherein if the second characteristic(s) of the captured particles is/are less than the second threshold, and at least one second characteristic is greater than a third threshold, the third threshold being less than the second threshold, the method further comprises the following additional steps:
   analyzing the first characteristic(s) of the detected particles so as to identify whether the lubricating liquid is polluted;
   cleaning the mechanical system if pollution of the lubricating liquid is identified; and
   scheduling regular collections of the particles captured by the capture device(s) if no pollution of the lubricating liquid is identified.

2. The method according to claim 1,
   wherein the method further comprises additional steps performed following the comparison step, if at least one first threshold is exceeded:
   analyzing the first characteristic(s) of the detected particles so as to identify whether the lubricating liquid is polluted;
   cleaning the mechanical system if pollution of the lubricating liquid is identified; and
   scheduling regular collections of the particles captured by the capture device(s) if no pollution of the lubricating liquid is identified.

3. The method according to claim 1,
   wherein an alarm is triggered after the mechanical system stops if at least one first threshold is exceeded.

4. The method according to claim 1,
   wherein, during the step of analyzing the first characteristic(s), presence of pollution of the lubricating liquid is identified if a variation over time of a first characteristic of the detected particles is an increasing curve with at least one change of slope, the slope decreasing with increasing time.

5. The method according to claim 1,
   wherein, during the step of analyzing the first characteristic(s), presence of pollution of the lubricating liquid is identified if a variation over time of a first characteristic of the detected particles includes a first increase over a first time interval, and then a plateau over a second time interval, or indeed if the variation includes a plurality of increases and a plurality of plateaus in succession.

6. The method according to claim 1,
   wherein, during the step of analyzing the first characteristic(s), no pollution of the lubricating liquid is identified if a variation over time of a first characteristic of the detected particles is constantly increasing in linear manner.

7. The method according to claim 1,
   wherein, during the step of analyzing the first characteristic(s), no pollution of the lubricating liquid is identified if a variation over time of a first characteristic of the detected particles is an increasing curve with at least one change of slope, the slope increasing with increasing time.

8. The method according to claim 1,
   wherein, when the mechanical system equips an aircraft, the method further comprises a step of transmitting the first characteristic(s) of the detected particles to a base on the ground in order to perform the step of analyzing the first characteristic(s).

9. The method according to claim 1,
   wherein a first characteristic of the detected particles is to be chosen from among the number, the size, and the flow rate of the particles, and wherein a second characteristic of the captured particles is to be chosen from among the number, the size, the mass, the material, and the morphology of the particles.

10. The method according to claim 1,
    wherein the step of measuring at least one first characteristic of detected particles flowing through at least one pipe of a lubrication circuit is limited to metal particles that are detected.

11. The method according to claim 1,
    wherein the step of measuring at least one first characteristic of detected particles flowing through at least one pipe of a lubrication circuit is limited to metal particles that are detected, and the step of analyzing the first characteristic(s) of the particles that are detected in order to identify whether the lubricating liquid is polluted is limited to the metal particles that are detected.

12. The method according to claim 1,
    wherein the step of collecting particles captured by the capture device(s) if at least one first threshold is exceeded is limited to the metal particles that are captured.

13. A monitoring system for monitoring a mechanical system, the monitoring system including a lubrication system for lubricating the mechanical system, the lubrication system being provided with:

at least one reservoir containing a lubricating liquid;

at least one lubrication circuit through which the lubricating liquid flows and which is designed to lubricate the mechanical system, the lubrication circuit(s) including pipes through which the lubricating liquid flows;

at least one flow generator for generating a flow of the lubricating liquid and making it possible to feed at least one lubrication circuit with the lubricating liquid; and at least one particle capture device;

wherein the monitoring system further includes at least one detection device for detecting particles that is arranged in at least one lubrication circuit as well as at least one computer and an alarm device, the monitoring system being configured to implement the method according to claim 1.

14. The monitoring system according to claim 13, wherein the particle capture device(s) include(s) at least one magnetic plug or at least one electric magnetic plug.

15. The monitoring system according to claim 13, wherein the lubrication system further includes at least one device that can trap the particles, the detection device being arranged upstream from the device(s) that can trap the particles.

16. The monitoring system according to claim 13, wherein at least one particle detection device is inductive, acoustic, or indeed optical.

17. A mechanical system including:

rotary elements;

elements for transmitting power and for reducing or increasing rotation speed; and the monitoring system;

wherein the monitoring system is the monitoring system according to claim 13.

18. The mechanical system according to claim 17, wherein the mechanical system is a power transmission main gearbox of an aircraft.

19. An aircraft including the mechanical system, wherein the mechanical system is the mechanical system according to claim 17.

20. A method of monitoring a mechanical system, the mechanical system including a lubrication system provided with:

a reservoir containing a lubricating liquid;

a lubrication circuit through which the lubricating liquid flows to lubricate the mechanical system, the lubrication circuit including a pipe through which the lubricating liquid flows;

a flow generator for generating a flow of the lubricating liquid to feed the lubrication circuit with the lubricating liquid; and a particle capture device;

wherein the method comprises:

measuring at least one first characteristic of detected particles flowing through the pipe of the lubrication circuit performed by a particle detection device;

comparing at least one first characteristic of the detected particles with a first threshold;

collecting particles captured by the capture device(s) if at least one first threshold is exceeded;

measuring at least one second characteristic of the captured particles;

comparing at least one second characteristic of the captured particles with a second threshold; and performing maintenance on the mechanical system if at least one second threshold is exceeded, wherein if the second characteristic(s) of the captured particles is/are less than the second threshold, and at least one second characteristic is greater than a third threshold, the third threshold being less than the second threshold, the method further comprises:

analyzing the first characteristic(s) of the detected particles so as to identify whether the lubricating liquid is polluted;

cleaning the mechanical system if pollution of the lubricating liquid is identified; and scheduling regular collections of the particles captured by the capture device(s) if no pollution of the lubricating liquid is identified, the particle detection device arranged in the pipe of each lubrication circuit of the lubrication system.

* * * * *